Figure 1:
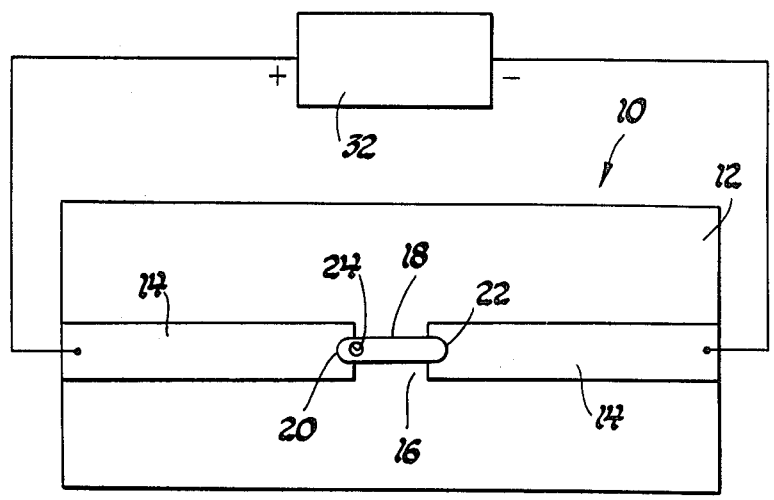

United States Patent [19]

Eesley et al.

[11] 4,281,533

[45] Aug. 4, 1981

[54] APPARATUS FOR MEASURING SOOT CONCENTRATION IN ENGINE OIL

[75] Inventors: Gary L. Eesley, Lake Orion; Gregory B. DeMaggio, St. Clair Shores; Jeffrey C. Buchholz, Detroit, all of Mich.

[73] Assignee: General Motors Corporation, Detroit, Mich.

[21] Appl. No.: 112,131

[22] Filed: Jan. 14, 1980

[51] Int. Cl.³ ...................... G01N 25/00; G01N 33/28
[52] U.S. Cl. .................................. 73/15 R; 73/61 R; 73/64
[58] Field of Search ............ 73/15 R, 61 R, 64, 359 R

[56] References Cited

U.S. PATENT DOCUMENTS 2,904,995  9/1959  Obermaier ............................ 73/359
3,049,964  8/1962  Miller et al. ............................ 73/64

Primary Examiner—Herbert Goldstein
Attorney, Agent, or Firm—Warren D. Hill

[57] ABSTRACT

Both junctions of a thin film thermocouple are formed on one side of a glass substrate. That side of the substrate is exposed to the diesel engine oil the soot content of which is to be measured. A light source on the other side of the substrate has its radiation directed through the substrate to a location at one of the junctions so that the light is absorbed by the oil adjacent that junction to a degree determined by its soot content. The temperature of the oil and the adjacent junction are increased by an amount dependent on the soot concentration and the thermocouple output is therefore a measure of the soot concentration in the engine oil.

3 Claims, 3 Drawing Figures

U.S. Patent

Aug. 4, 1981

4,281,533

APPARATUS FOR MEASURING SOOT CONCENTRATION IN ENGINE OIL

This invention relates to apparatus for measuring the soot content of engine oil by optically induced heating.

The combustion process in diesel engines produces quantities of soot some of which finds its way into the engine oil. The soot reduces the effectiveness of the engine oil if the soot is allowed to accumulate to high concentrations. In practice, such high concentrations are avoided by frequent changes of the engine oil determined by a schedule of fixed service intervals. It is desirable, however, to monitor the actual soot concentration to determine when engine oil should be changed thereby avoiding premature oil changes as well as avoiding unacceptably high concentrations of soot.

It is therefore a general object of this invention to provide an apparatus for measuring of the soot concentration of engine oil and particularly such an apparatus using optically induced heating of the oil.

The invention is carried out by an apparatus comprising a thin film thermocouple on a substrate with both junctions exposed to the engine oil, a radiation source projecting radiation onto the oil adjacent one junction to locally heat that oil and junction by an amount depending on the soot content of the oil and a circuit for measuring the thermocouple voltage.

Figure 2:
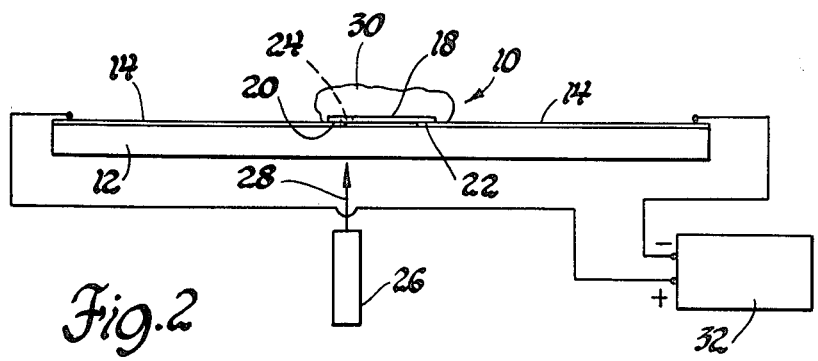
Figure 3:
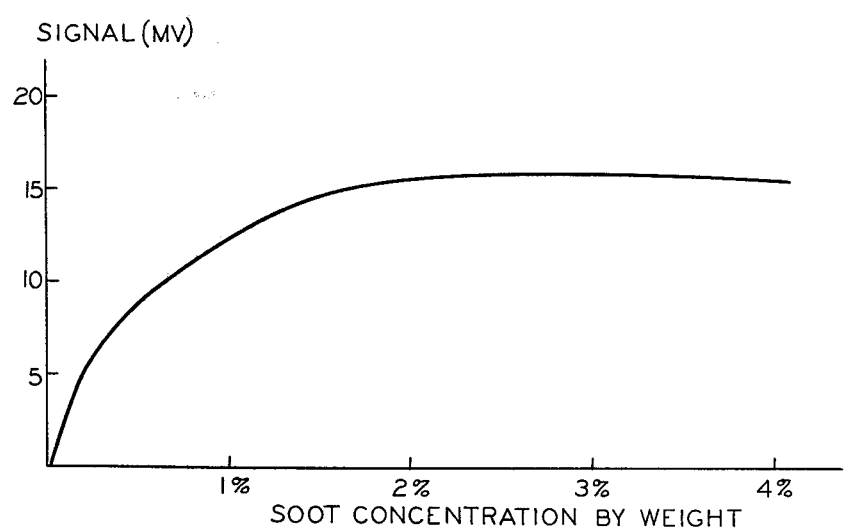

The above and other advantages will be made more apparent from the following specification taken in conjunction with the accompanying drawings wherein like reference numerals refer to like parts and wherein:

FIG. 1 is a plan view of a thermocouple device used for measuring soot concentration according to the invention, FIG. 2 is an elevational view of the device of FIG. 1, and FIG. 3 is a graph of thermocouple current versus soot concentration as measured by the apparatus according to the invention.

Referring to FIGS. 1 and 2, an apparatus for measuring the soot concentration in engine oil includes a thermocouple 10 formed on a glass substrate 12 having formed thereon a pair of pathways 14 of constantan film approximately 1,000 Å thick. These pathways are separated by a gap 16 which is bridged by a copper film 18 of about the same thickness which slightly overlaps the pathways 14 to define thermocouple junctions 20 and 22 spaced by the width of the gap 16. The gap may be, for example, four millimeters or more in width. A hole 24 is formed in the films 14 and 18 at the junction 20. As shown in FIG. 2, a light source such as a laser 26 projects a beam 28 of radiation through the hole 24. The light source 26 is placed on the side of the substrate opposite the thin film thermocouple junctions while the side of the substrate containing the junctions is immersed in the oil 30, the soot content of which is to be measured. The illustrated body of oil 30 is representative of any oil volume and preferably is an oil stream circulating in an engine. An indicator or detector circuit 32 is connected across the conductors 14 to measure the thermocouple voltage.

The circuit 32 is preferably a voltmeter where a direct readout of the voltage is desired whereas a detector circuit such as a level detector is used to provide an output when a preset thermocouple output voltage is attained. A warning device energized by the detector output would indicate to an operator that a prescribed soot concentration has been reached. The source 26 has radiation such that the substrate 12 as well as clean engine oil is transparent to the radiation while any soot contained in the oil absorbs the radiation. The radiation from the source 26 is directed onto the portion of the oil which is immediately adjacent the junction 20 so that any temperature rise of the oil in that region due to absorption of the light will be measured by the thermocouple. Any bulk heating affect of the oil such as caused by heating of the engine equally affects both thermocouple junctions so that it causes no thermocouple output. The only thermocouple output is due to the selective heating at the junction 20 by the light incident on and absorbed by the oil adjacent the junction. The hole 24 in the junction 20 couples the light to the oil 30 at that point. Where the source 26 is a laser the light is conveniently focused through the hole 24 into the oil and the radiation does not fall directly on the junction 20. It is not necessary that the source 26 be a laser, rather a white light source properly focused through the hole 24 is useful as well.

FIG. 3 is a graph indicating thermocouple output voltage plotted against soot concentration in diesel engine oil. In obtaining the data for the FIG. 3 graph, the light source was a two milliwatt helium-neon laser having a wavelength of 6328 Å. Similar results are obtained using a 10 milliwatt helium-cadmium laser having a wavelength of 4416 Å or a white light microscope lamp. As seen in the graph, the thermocouple produces a distinguishable voltage output for various soot concentrations of up to about 2% by weight of the engine oil. Thus, as the soot concentration increases, the temperature rise at the thermocouple junction 20 also increases producing a larger signal voltage which is the net thermocouple voltage. Except for very clean oil, most of the light power transmitted through the hole 24 will be eventually absorbed but only the temperature rise in oil close to the junction 20 contributes to the signal. Thus, oil samples having a high concentration of soot contains most of the temperature rise within one millimeter or less of the junction. Since soot absorbs all visible wavelengths of light many types of light sources may suffice as the light source so long as the substrate and clean oil are transparent to the radiation. The invention is not limited, however, to sources of visible light since other wavelengths which are absorbed by the soot are useful. Further advantages of the thermocouple structure described herein is that the thermocouple surfaces will clean readily when new oil is installed and the thermocouples are fabricated inexpensively.

Of course, many configurations of the test device are possible since various thermocouple structures and geometries may be used. The substrate 12 may, for example, form a wall portion of an oil reservoir with the radiation source 26 located outside the reservoir. On the other hand, the entire apparatus may be immersed within the reservoir if the radiation source 26 is protected from the oil or the radiation is somehow introduced to the oil adjacent the junction 20 in spite of the presence of oil.

It will thus be seen that the apparatus according to this invention is useful to provide a measurement of engine oil soot concentration both reliably and inexpensively.

The embodiments of the invention in which an exclusive property or privilege is claimed are defined as follows:

1. Means for measuring soot concentration in engine oil comprising
   a thin film thermocouple formed on one side of a transparent substrate and having first and second spaced junctions, the side of the substrate bearing the thermocouple being immersed in oil,
   means for heating the oil adjacent the first junction by an amount dependent on the soot concentration, the heating means including a source of radiation to which the substrate as well as clean oil is substantially transparent and which is absorbed by soot, and means for passing the radiation therefrom through the substrate into the oil adjacent the first junction whereby the first junction is heated when soot is present in the oil,
   and means for measuring the thermocouple net voltage which is a measure of the soot concentration in the oil.

2. Means for measuring soot concentration in engine oil comprising,
   means for heating oil in a local zone including a source of radiation directed into the local zone whereby soot in the oil absorbs the radiation and heats the oil by an amount dependent on the soot concentration,
   means for measuring the oil temperature increase due to the absorbed radiation comprising a thin film thermocouple formed on a substrate and having first and second spaced junctions immersed in the oil, the first junction being disposed in intimate heat transfer relation to the oil in the local zone so that the first junction is affected by the said oil temperature increase and the second junction is essentially unaffected by the temperature increase to thereby generate a thermocouple voltage corresponding to the temperature increase,
   and means for measuring the thermocouple net voltage which is a measure of the soot concentration in the oil.

3. Means for measuring soot concentration in engine oil comprising,
   means for heating oil in a local zone including a source of radiation directed into the local zone whereby soot in the oil absorbs the radiation and heats the oil by an amount dependent on the soot concentration,
   means for measuring the oil temperature increase due to the absorbed radiation comprising a thin film thermocouple formed on one side of a substrate transparent to the said radiation and having first and second spaced junctions immersed in the oil, the radiation source being on the other side of the substrate for projecting radiation through the substrate toward the local zone, and means comprising an aperture in the first junction for coupling the radiation into the oil in the local zone, the first junction being disposed in intimate heat transfer relation to the oil in the local zone so that the first junction is affected by the said oil temperature increase to generate a corresponding thermocouple voltage,
   and means for measuring the thermocouple net voltage which is a measure of the soot concentration in the oil.

* * * * *